(12) United States Patent
Smit et al.

(10) Patent No.: US 10,072,099 B2
(45) Date of Patent: Sep. 11, 2018

(54) PROCESS FOR THE ORGANOSOLV TREATMENT OF LIGNOCELLULOSIC BIOMASS

(71) Applicant: Stichting Energieonderzoek Centrum Nederland, Petten (NL)

(72) Inventors: Adrianus Theodorus Smit, Petten (NL); Wouter Johannes Joseph Huijgen, Petten (NL); Rudie Johan Hendrik Grisel, Petten (NL)

(73) Assignee: Stichting Energieonderzoek Centrum Nederland, Petten (NL)

( * ) Notice: Subject to any disclaimer, the term of this patent is extended or adjusted under 35 U.S.C. 154(b) by 0 days.

(21) Appl. No.: 14/905,258

(22) PCT Filed: Jul. 15, 2014

(86) PCT No.: PCT/NL2014/050481
§ 371 (c)(1),
(2) Date: Jan. 14, 2016

(87) PCT Pub. No.: WO2015/009145
PCT Pub. Date: Jan. 22, 2015

(65) Prior Publication Data
US 2016/0152736 A1    Jun. 2, 2016

(30) Foreign Application Priority Data

Jul. 15, 2013  (NL) .................................. 2011164

(51) Int. Cl.
| | |
|---|---|
| *C08B 15/08* | (2006.01) |
| *C08H 8/00* | (2010.01) |
| *C12P 19/02* | (2006.01) |
| *D21C 3/20* | (2006.01) |
| *C07G 1/00* | (2011.01) |
| *C12P 19/14* | (2006.01) |
| *C13K 1/02* | (2006.01) |
| *D21C 3/00* | (2006.01) |

(52) U.S. Cl.
CPC ............ *C08B 15/08* (2013.01); *C07G 1/00* (2013.01); *C08H 8/00* (2013.01); *C12P 19/02* (2013.01); *C12P 19/14* (2013.01); *C13K 1/02* (2013.01); *D21C 3/003* (2013.01); *D21C 3/20* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 2,022,654 A | 12/1935 | Dreyfus | |
| 4,470,851 A | 9/1984 | Paszner et al. | |
| 2009/0061495 A1* | 3/2009 | Beatty | C12P 7/10 435/165 |

FOREIGN PATENT DOCUMENTS

| | | |
|---|---|---|
| EP | 2 336 193 A1 | 6/2011 |
| WO | WO-03/062430 A1 | 7/2003 |
| WO | WO-2007/120210 A2 | 10/2007 |
| WO | WO-2008/041840 A1 | 4/2008 |
| WO | WO-2010/074577 A1 | 7/2010 |
| WO | WO-2011/097720 A1 | 8/2011 |
| WO | WO-2012/000093 A1 | 1/2012 |
| WO | WO-2015/009145 A1 | 1/2015 |

OTHER PUBLICATIONS

Huijgen et al., "Pretreatment and fractionation of wheat straw by an acetone-based organosolv process", Industrial & Engineering Chemistry Research, 2010, vol. 49, No. 20, pp. 10132-10140.
Perez et al., "Selective acetone-water delignification of *Eucalyptus urograndis*: An alternative towards the biorefinery approach", The Open Agriculture Journal, 2010, vol. 4, pp. 145-152.
Ghose, "Measurement of cellulose activities", Pure & Applied Chemistry, vol. 59, 1987, No. 2, pp. 257-268.
Huijgen et al. "Fractionation of wheat straw by prehydrolysis, organosolv delignification and enzymatic hydrolysis for production of sugars and lignin" Bioresource Technology, 2012, vol. 114, pp. 389-398.
International Search Report issued in International Patent Application No. PCT/NL2014/050481 dated Sep. 17, 2014.
Abdul Khalil, H.P.S. et al., "Peer-reviewed article chemical composition, anatomy, lignin distribution, and cell wall structure of Malaysian plant waste fibers introduction", Bioresources 1(2), Nov. 4, 2006, pp. 220-232.
Abels et al., "Membrane processes in biorefinery applications", Journal of Membrane Science, 2013, vol. 444, pp. 285-317.
Hariharan et al., "Peer-reviewed article optimization of lignin peroxidate, manganese peroxidase, and lac production from ganoderma lucidum under solid state fermentation of pineapple leaf introduction", BioResources, Nov. 26, 2012, pp. 250-271.
Cybulska, I. et al., "Catalyzed modified clean fractionation of prairie cordgrass integrated with hydrothermal post-treatment", Biomass and Bioenergy, vol. 46, Nov. 1, 2012, pp. 389-401.
Gong et al., "Development of an integrated pretreatment fractionation process for fermentable sugars and lignin: Application to almond () shell*", Biomass and Bioenergy, Pergamon, Amsterdam, NL, vol. 35, No. 10, Aug. 24, 2011, pp. 4435-4441.

(Continued)

*Primary Examiner* — Michelle F Paguio Frising
(74) *Attorney, Agent, or Firm* — Gilberto M. Villacorta; Sunit Talapatra; Foley & Lardner LLP (57) ABSTRACT

The present invention is directed at a process for fractionating lignocellulosic biomass for the purpose of reducing processing costs, increasing delignification, reducing side-reactions, in particular reducing hemicelluloses degradation, improving cellulose hydrolysis and increasing the nativity of the obtained lignin, by performing organosolv fractionation of the biomass with a treatment liquid at a temperature below 170° C., wherein the treatment liquid comprises a non-hydroxylic organic solvent, in particular a ketone, water and some acid, and optionally subjecting the cellulose-enriched product stream to enzymatic hydrolysis.

19 Claims, 1 Drawing Sheet

(56) References Cited

OTHER PUBLICATIONS

Garcia et al., "Energy and economic assessment of soda and organosolv biorefinery processes", Biomass and Bioenergy, 2010, pp. 1-10.

Gonzalez Alriols et al., "Combined organosolv and ultrafiltration lignocellulosic biorefinery process", Chemical Engineering Journal, 2009, pp. 1-8.

Huijgen et al., "Fractionation of what straw by prehydrolysis, organosolv delignification and enzymatic hydrolysis for production of sugars and lignin", Bioresource Technology, vol. 114, Mar. 7, 2012, pp. 389-398.

International Search Report issued in International Patent Application No. PCT/EP2016/053271, dated May 18, 2016.

International Search Report of PCT/NL2014/050095 dated Apr. 16, 2014.

Li et al., "Formic acid based organosolv pulping of bamboo (): Comparative characterization of the dissolved lignins with milled wood lignin", Chemical Engineering Journal, Elsevier Sequoia, Lausanne, CH, vol. 179, Oct. 20, 2011, pp. 80-89.

Nordin et al., "Chemical elemental characteristics of biomass fuels", Biomass and Bioenergy, Pergamon, Amsterdam, NL, vol. 6, No. 5, Jan. 1, 1994, pp. 339-347.

Omojasola, P.F. et al., "Cellulase production by some fungi cultured on pineapple waste", Nature and Science, 6(2), Jan. 1, 2008, pp. 64-79.

Papatheofanous, M.G. et al., "Two-stage acid-catalyzed fractionation of lignocellulosic biomass in aqueous ethanol systems at low temperatures", Bioresource Technology 54, Issue 3, Jan. 1, 1995, pp. 305-310.

Phillips, M. et al., "The chemistry of lignin. IX. Lignin from Barley Straw", Journal of the American Chemical Society, vol. 56, Dec. 1, 1934, pp. 2707-2710.

Sun, F. et al., "Enhanced enzymatic hydrolysis of wheat straw by aqueous glycerol pretreatment", Bioresource Technology, Elsevier BV, GB, vol. 99, No. 14, Sep. 1, 2008, pp. 6156-6161.

Wildschut et al., "Ethanol-based organosolv fractionation of wheat straw for the production of lignin and enzymatically digestible cellulose", Bioresource Technology, 2013, vol. 135, pp. 58-66.

Zhang et al., "Organosolv pretreatment of plant biomass for enhanced enzymatic saccharification", Green Chemistry, Jan. 2016, pp. 1-23.

Zhao et al., "Organosolv pretreatment of lignocellulosic biomass for enzymatic hydrolysis", Appl. Microbiol Biotechnol, 2009, vol. 82, pp. 815-827.

* cited by examiner

PROCESS FOR THE ORGANOSOLV TREATMENT OF LIGNOCELLULOSIC BIOMASS

CROSS-REFERENCE TO RELATED APPLICATIONS

This application is the National Phase of International Patent Application No. PCT/NL2014/050481, filed Jul. 15, 2014, published on Jan. 22, 2015 as WO 2015/009145 A1, which claims priority to Netherlands Patent Application No. 2011164, filed Jul. 15, 2013. The contents of these applications are herein incorporated by reference in their entirety.

The present invention relates to an improved process for the fractionation of lignocellulosic biomass using organosolv.

BACKGROUND

Biomass, especially lignocellulosic biomass, is a valuable resource for the production of (bio)fuels, chemicals, performance products and energy. Lignocellulose is the most abundant renewable biomass available on land, and therefore relatively cheap. It comprises mainly cellulose, hemicellulose and lignin. Many research efforts have been devoted to the development of processes for the cost-effective conversion of biomass, especially lignocellulosic biomass, to valuable compounds. An example thereof is the conversion of cellulose to glucose, which in turn may serve e.g. as a precursor for 'second-generation' bioethanol (e.g. by fermentation of glucose), and is thus suitable for the production of biofuels.

The main structural components of biomass are cellulose (a glucan), hemi-cellulose and lignin. The two major types of hemicellulose are xylans and (gluco)-mannans. Xylans have xylose ($C_5$ sugar) backbones, sometimes substituted with arabinose or glucuronic acid side groups, and are predominant in hardwood and grasses, while (gluco)mannans have backbones with a glucose:mannose (both $C_6$ sugars) ratio of about 1:3, sometimes substituted with galactose side groups, and are predominant in softwood. Minor hemicellulose types include xyloglucans and arabino-galactans. Hemicelluloses may be chemically linked to lignin. Table 1 below gives approximate compositions of some biomass types.

TABLE 1

Compositions of the structural components of some biomass types (in wt % based on dry weight)

|  | glucan | mannan | xylan | other polysaccharides | lignin |
| --- | --- | --- | --- | --- | --- |
| softwood | 35-40 | 15-20 | 5-10 | 3-10 | 25-32 |
| hardwood | 40-50 | 1-4 | 15-30 | 2-5 | 22-30 |
| grasses, straws | 33-40 | 0-2 | 20-27 | 3-8 | 20-32 |

The so-called organosolv process can be used to treat biomass (pretreatment), in order to make cellulose polymers better accessible for hydrolytic enzymes converting cellulose to glucose, or for pulping or fractionating of the biomass. Without pre-treatment, the cellulose within lignocellulosic biomass is poorly accessible for the hydrolytic enzymes, as it is shielded by other structural components in the biomass, such as lignin and hemicelluloses. Conventional organosolv involves high-temperature treatment (typically between 180 and 220° C.) of the biomass with a (water-miscible) organic solvent (e.g. ethanol) and optionally an (acidic) catalyst. During organosolv fractionation, the lignocellulose biomass is fractionated into a cellulose-enriched solid product stream (pulp) and a liquid product stream (liquor) comprising dissolved lignin and hemicellulose derivatives.

The hemicelluloses present in the lignocellulosic biomass are relatively unstable and break down during organosolv. Hemicellulose is first hydrolysed to sugar monomers ($C_5$ and/or $C_6$ sugars), which may subsequently dehydrate to furans such as furfural and/or react further to other compounds (including xylosides and condensation products with lignin ("pseudo-lignin")). Most of these latter compounds are considered less valuable, with a smaller demand for in the market, than hemicellulose itself or the products directly obtained from it such as monomeric sugars (mainly xylose, mannose and glucose). Degradation products may be part of the cellulose stream and/or the lignin stream, which are produced by the organosolv process, thereby reducing their purity and the efficiency of further treatment of these streams to produce valuable end-products, such as ethanol. In addition, potentially valuable compounds that can be derived from the hemicellulose (e.g. monomeric sugars and furfural) get lost, thus reducing the effectiveness of the conversion of biomass into valuable components.

Also, the cellulose-enriched product stream obtained from the organosolv process comprises impurities. Although organosolv treatment separates large parts of lignin and hemicellulose from the cellulose pulp, the cellulosic pulp typically still comprises significant amounts of lignin, as well as pseudo-lignins. The latter may be formed during organosolv fractionation by reaction of lignin with e.g. proteins, other extractives and/or furans such as furfural. These impurities hamper the enzymatic hydrolysis of cellulose to glucose, which is to date still not feasible on a commercial scale, since it cannot compete yet with glucose produced from first generation biomass sources (starch, sucrose etc.), in view of the high costs of the pretreatment step and required amounts of enzyme. Alternatives to enzymatic hydrolysis of cellulose, e.g. concentrated acid treatment, are undesirable for environmental reasons, corrosion of equipment and associated costs, and they are typically less selective towards glucose because of enhanced sugar degradation reactions. Hence, one of the challenges of current research is to find means to enhance the efficiency of pretreatment of biomass and (simultaneously) improve the enzymatic hydrolysis of cellulose, in order to allow application on an industrial scale.

WO 2007/120210 describes organosolv treatment of biomass at about 120-220° C., at a pH of less than about 4, and with ethanol as preferred solvent. The organosolv reaction is performed at 170° C. and subsequent separation of the solids from the liquids by filtration is performed at 130° C. WO 2012/000093 and WO 2011/097720 describe organosolv treatment of biomass at 130-170° C., at a pH of 1.5-2.5, and with ethanol comprising 1.5-2.5 wt % acid as preferred solvent. Da Silva Perez and Curvelo (*Open Agriculture Journal* 2010, 4, 145-152) studied the kinetics of acetone-water delignification of *Eucalyptus urograndis* at temperatures ranging from 145 to 195° C. and found that at the lower temperatures the least efficient delignification occurred. Huijgen et al. (*Ind. Eng. Chem. Res.* 2010, 49, 10132-10140) describe acetone-based organosolv of wheat straw at temperatures ranging from 160 to 220° C., in the absence of an acid.

SUMMARY OF THE INVENTION

The invention relates to an advanced organosolv process of lignocellulosic biomass, resulting in a cellulose-enriched product (pulp) containing less impurities and a lignin-enriched product containing a higher content of native lignin. Surprisingly, the inventors have found that the organosolv process can be efficiently performed at reduced temperatures, such as below 170° C., preferably between 100° C. and 170° C., when a non-hydroxylic organic solvent is used as a solvent.

Performing organosolv at such reduced temperatures is especially desirable for two reasons. First of all, it reduces the costs of the pretreatment step, and secondly it reduces degradation of valuable hemicellulose derivatives. Such reduction of costs is particularly important in the current strive for sustainability, and provides a reduction in energy consumption (lower heat demand), reduction in pressure during the organosolv reaction, a reduced degree of corrosiveness of the medium in view of the lower temperature. As discussed above, degradation of hemicellulose derivatives during pretreatment significantly reduces the effectiveness of the conversion of biomass into valuable components. On the other hand, at those reduced temperatures, non-structural organic components (e.g. proteins, ash, lipids and other extractives) present in biomass may negatively affect the organosolv process. During high temperature organosolv (i.e. above 170° C.), the non-structural components of the biomass decompose or react with structural components. The process according to the invention circumvents these undesirable side-reactions of non-structural organic components to a large extent, and the organosolv process operates more smoothly, even at reduced temperatures. This is especially important for the low temperature organosolv process of herbaceous biomass or annual fibres, such as straw, which comprise significant amounts of apolar non-structural organic components, such as fatty acids and waxy materials. At the temperatures employed during low temperature organosolv, these apolar components may hamper efficient fractionation by forming aggregates during the organosolv process, which is observed when e.g. ethanol is used as solvent. Thus, the process according to the invention is especially suitable for organosolv of herbaceous biomass or annual fibre. A further advantage of working at reduced temperatures is the reduced degradation of lignin. During high temperature organosolv, lignin, especially the phenolic moieties, may react with non-structural components in the biomass or hemicellulose degradation products, to form pseudo-lignins.

The inventors have surprisingly found that performing organosolv, especially low temperature organosolv, with a non-hydroxylic organic solvent, results in efficient delignification of the biomass together with a reduction of side-reactions and thus in formation of less impurities. Delignification is surprisingly efficient at such reduced temperatures of below 170° C., without significantly increasing the required content of the acid catalyst. Although high acid concentrations in the treatment liquid of an organosolv step, well above 100 g or 250 g per kg biomass, are known to lower the required temperature for fractionation, such high acid concentrations are highly undesirable for causing corrosion problems and environmental concerns. Moreover, organosolv reaction in high (organic) acid concentration does not provide the desired reduction in costs of the organosolv process, in view of increased equipment and waste disposal costs.

A further advantage of the process of the invention is de reduced occurrence of side-reactions. Without wishing to be bound to any theory, it is believed that the presence of hydroxyl moieties (OH groups) makes the organic solvent reactive towards structural components of the biomass, such as towards the monomeric sugar moieties and towards lignin. As a result thereof, conversion of sugar monomers such as glucose and xylose to glucosides and xylosides occurs, which is undesirable because it lowers the overall yield of monomeric sugar moieties after organosolv and after (enzymatic) hydrolysis of the pulp. Such undesirable side-reactions may also occur on oligomeric or polymeric carbohydrates, and give rise to the formation of glucosides and xylosides after (enzymatic) hydrolysis of the carbohydrate. Also, more pseudo-lignins are formed during organosolv with hydroxylic organic solvents, wherein native lignin has reacted with solvent molecules at their OH group. An additional advantage of this reduction of side-reactions is that less solvent is lost during organosolv, which renders organosolv with non-hydroxylic organic solvents more efficient than with hydroxylic organic solvents. On the other hand, solvent may be lost by self-condensation during organosolv, which may occur for e.g. ketone solvents such as acetone (e.g. via aldol condensation) as well as for hydroxylic solvents such as ethanol (e.g. by ether formation). Notably, hardly any self-condensation of the non-hydroxylic solvents is observed during low temperature organosolv process (data not shown), which renders these solvents suitable for use in the process according to the invention.

DETAILED DESCRIPTION

The invention relates to a process for fractionating lignocellulosic biomass into a cellulose-enriched product stream (pulp) and a lignin-enriched product stream (liquor), comprising subjecting optionally pre-extracted biomass to an organosolv step using a non-hydroxylic solvent. Without being bound by a theory, it is believed that alcoholic solvents such as ethanol are more reactive towards the structural components of biomass, as such giving rise to undesirable side-reactions. Because of the reduced side-reactions, the process according to the invention affords cleaner product streams, which is desirable in view of efficient biomass valorisation, but also renders the subsequent enzymatic hydrolysis of the cellulose pulp more efficient.

The process according to the invention is referred to as low temperature organosolv, i.e. organosolv performed at a temperature below 170° C., preferably even lower as defined below. In the context of the present invention, "organosolv" may also be referred to as "fractionation", which terms are used interchangeably. The process according to the invention may also be referred to as "biomass pretreatment", which involves the step of low temperature organosolv, but may include further steps such as pre-extraction and enzymatic hydrolysis of the cellulose-enriched product stream (pulp).

Thus, the invention relates to a biomass fractionation process, comprising the step of treating the biomass with a treatment liquid at a temperature below 170° C., wherein the treatment liquid comprises at least 20 wt % of a non-hydroxylic organic solvent, at least 5 wt % of water and an acid. The amount of the acid can be defined as a concentration by weight, i.e. between 0.01 wt % and 2.0 wt %, based on total weight of the treatment liquid. Alternatively, the amount of acid can be defined as acid equivalents, i.e. between 2 and 400 meq of an acid having a pKa of 4.5 or lower, a meq being defined as a mmol of hydrogen ions per L of treatment liquid. As a further alternative, the amount of acid can be defined in relation to the amount of biomass treated, i.e. 1-250 g acid or 10 mmol-2.5 mol acid per kg of biomass (dry weight), wherein 1 L of treatment liquid is used per 20-10000 g dry weight of biomass.

Biomass

Biomass suitable for the process according to the invention includes ligno-cellulosic biomass, such as softwood, hardwood, and herbaceous biomass, including grasses and straws, and can be supplied in the form of forestry residues, agricultural residues, yard waste, animal and human waste (e.g. biodegradable municipal waste). Such biomass comprises in general 20 to 80 wt.% carbohydrates (based on dry matter), which are valuable starting materials for production of fuels and chemicals (e.g. in a biorefinery process). Lignocellulosic biomass (so-called second generation biomass) is cheaper than starch-containing biomass (first generation biomass) and does not compete with (human) dietary needs. Preferably, the biomass comprises herbaceous biomass. Preferably, herbaceous biomass in the form of agricultural residues and/or biodegradable municipal waste is used in the process according to the invention, more preferably, the herbaceous biomass is selected from biodegradable municipal waste, straw, leaves, grasses and combinations thereof, most preferably straw (e.g. rice straw, barley straw, wheat straw). Preferably, the biomass has a lignin content of at least 5 wt %, more preferably at least 10 wt %, such as 20-35 wt %, based on total dry weight of the biomass.

The biomass subjected to the process according to the invention may be fresh or dried biomass, optionally after removal of large impurities such as stones and pieces of metal, and optionally chopped or milled to pieces for ease of handling (e.g. pieces of 0.01 to 50 cm, in particular 0.1-10 cm in length or diameter, depending on the type of biomass). Unless indicated otherwise, amounts of biomass are defined below on the basis of dry weight.

Organosolv

The organosolv process step separates the lignocellulose biomass into a cellulose-enriched product stream (also referred to as 'cellulose pulp' or just 'pulp') and a lignin-enriched product stream (liquor). The organosolv step of the process according to the invention is performed at a temperature below 170° C., preferably between 100° C. and 170° C., more preferably between 100° C. and 160° C., or between 120° C. and 165° C., even more preferably between 130° C. and 160° C., most preferably between 130° C. and 150° C. In specific embodiments the organosolv process is performed at temperature below 140° C., preferably between 100° C. and 139° C., more preferably between 120° C. and 135° C. It was found that low temperature organosolv, i.e. at a temperature below 170° C., can only be efficiently performed when acid-catalysed. The higher the temperature, the greater the extent of self-condensation of the solvent, giving rise to undesirable solvent loss, while lower temperatures lead to inferior fractionation and reduced delignification. The inventors found that the above temperature ranges provide optimal results in that no or hardly any solvent self-condensation is observed, while delignification remains high. The organosolv process step may be performed at any pressure as known in the art, which typically is about 1 to 50 bar (absolute). The duration of the organosolv process step may be any time suitable to effectuate the fractionation, as will be appreciated by the skilled person. Typical duration of the organosolv process is from 30 to 150 minutes.

Typically, the suspension of biomass and treatment liquid is obtained by mixing at most 50 L and at least 0.1 L of treatment liquid per kg dry weight of the biomass, preferably between 1.0 L and 20 L, most preferably between 3 L and 15 L. Thus organosolv treatment of biomass uses 1 L of treatment liquid as defined below per between 20 g and 10 kg of biomass, preferably per between 50 and 1000 g, most preferably per between 67 and 333 g of biomass (dry weight). The optimum ratio of treatment liquid to biomass will depend on the type of biomass. For procedural economy, the liquid to solid weight ratio (L/S) of the organosolv step is preferably as low as possible, preferably lower than 20/1, more preferably lower than 12/1, even more preferably lower than 8/1, most preferably lower than 6/1. In one embodiment, the L/S ratio is at least 0.5/1, preferably at least 1/1, even more preferably at least 1.5/1, most preferably at least 2/1. To further increase the efficiency of the process, (part of) the solvents may originate from a recycled waste stream of an earlier organosolv process, typically from a purified organosolv liquor.

The treatment liquid comprises at least one non-hydroxylic organic solvent. The non-hydroxylic organic solvent used in the treatment liquid may be a non-hydroxylic single solvent, but also encompasses mixtures of non-hydroxylic organic solvents. Suitable non-hydroxylic organic solvents include all organic solvents which are known in the art to be suitable for organosolv, except all hydroxylic solvents. Especially polar non-hydroxylic solvents are suitable. In the context of the present invention, "hydroxylic solvents" comprise at least one hydroxyl moiety (OH group), such as alcohols or "alcoholic solvents" comprising one or more hydroxyl moieties bound to a carbon atom (directly or indirectly through S, O, N or another atom), such as methanol, ethanol, (iso)propanol, butanol, ethylene glycol, methoxyethanol, or organic solvents comprising a carboxylic acid moiety (COOH group), such as formic acid, acetic acid, peracetic acid and haloacetic acids. The presence of large amounts of acid during organosolv is highly undesirable, as this may cause heavy corrosion of the equipment and reactor. However, a catalytic amount of acid should be present in addition to the non-hydroxylic organic solvent, as described below.

A compound is considered to be a solvent in the context of the present invention, when it is liquid under the process conditions of the organosolv reaction, preferably when it is liquid under ambient conditions. It is preferred that the solvent has a sufficiently low boiling point to enable easy work-up by distillation or any other means of separation. More procedural efficiency, it is preferred that the organic solvent is recycled to the organosolv reactor for a further organosolv step after it has been removed from organosolv liquor. Such removal is conveniently accomplished by distillation, for which it is preferred that the boiling point of the organic solvent is below that of water, which is also present in the liquor. Thus, the non-hydroxylic organic solvent preferably has a boiling point below 100° C., more preferably below 90° C., even more preferably between 30° C. and 85° C., most preferably between 45° C. and 80° C. Moreover, the solvent should not be apolar, since lignin hardly dissolves in such solvents, and hence hydrocarbons and non-polar halogenated hydrocarbons are not suitable. Apolar solvents may be present in the treatment liquid as a minor component in addition to the (polar) non-hydroxylic solvent, preferably less then 5 wt % based on total weight of the treatment liquid, most preferably apolar solvents such as hydrocarbons or not present at all.

In particular, a suitable non-hydroxylic organic solvent should contain at least an oxygen and/or nitrogen-containing function (ether, ketone, ester, amine, amide, imide, cyanide, nitro), especially a function at least containing an oxygen atom, such as in ethers, ketones, esters and amides. Preferably, the non-hydroxylic solvent comprises an ether moiety and/or a carbonyl moiety, such as a ketone moiety, an ester moiety or an amide moiety, more preferably the non-hydroxylic solvent comprises at least a ketone moiety and optionally one or more selected from an ether moiety, an ester moiety or an amide moiety. Preferably, the non-hydroxylic organic solvent is selected from ethers and ketones, more preferably the non-hydroxylic organic solvent is a ketone. Ketones are especially preferred in view of the high solubility of lignin in ketone solvents. Preferred ethers include dimethoxyethane, tetrahydrofuran (THF), 1,4-dioxane and 1,3-dioxolane. Preferred ketones include acetone, butanone (=methyl ethyl ketone or MEK), methyl isobutyl ketone (MIBK), cyclohexanone, acetoacetic (3-oxobutanoic) acid esters, and levulinic (4-oxopentanoic) esters, such as methyl levulinate and ethyl levulinate. Preferred esters include $C_3$-$C_5$ esters such as ethyl acetate.

In an especially preferred embodiment, the non-hydroxylic organic solvent is selected from the group consisting of acetone, butanone, ethyl levulinate and mixtures thereof, more preferably selected from the group consisting of acetone, butanone and mixtures thereof, or alternatively selected from the group consisting of acetone and ethyl levulinate, even more preferably the non-hydroxylic organic solvent comprises acetone or a mixture of acetone and butanone, most preferably the non-hydroxylic organic solvent is acetone. Alternatively, the non-hydroxylic organic solvent comprises a mixture of acetone and butanone, preferably is a mixture of acetone and butanone. In case the non-hydroxylic organic solvent comprises a mixture of acetone and butanone, the weight ratio of butanone to acetone is preferably 10/1-1/5, more preferably 5/1-1/2, most preferably 3/1-1/1. Preferably, the treatment liquid comprises at least 10 wt % of the non-hydroxylic organic solvent, more preferably between 20 wt % and 80 wt %, even more preferably between 20 wt % and 70 wt % even more preferably between 25 wt % and 70 wt % or between 20 wt % and 60 wt %, most preferably between 30 wt % and 60 wt %. Here, wt % values of non-hydroxylic solvent are given based on total weight of the solvents (i.e. non-hydroxylic solvent, water and optionally minor amounts of hydroxylic solvent) in the treatment liquid.

The treatment liquid further comprises water, and optionally other organic solvents, in addition to the non-hydroxylic organic solvent. The presence of water in the treatment liquid allows hydrolysis reactions to take place during organosolv, in order to break up the network of structural components. It should be noted that such hydrolysis takes place at the covalent bonds between e.g. lignin and hemicellulose, and not necessarily between the sugar monomers within a polysaccharide chain such as cellulose. Preferably, the treatment liquid comprises at least 5 wt % water, more preferably at least 10 wt %, even more preferably between 20 wt % and 80 wt % water, even more preferably between 30 wt % and 75 wt % water, most preferably between 40 wt % and 70 wt % water. The weight ratio of organic solvent(s) (i.e. the non-hydroxylic organic solvent(s) and optionally any other organic solvent) to water is preferably between 20/80 and 80/20, more preferably between 30/70 and 75/25, even more preferably between 40/60 and 70/30, even more preferably between 40/60 and 65/35, more preferably between 40/60 and 60/40. The higher amounts of water, such as at least 20 wt %, at least 30 wt % or even at least 40 wt %, and/or the lower amounts of non-hydrolytic solvent, such as at most 80 wt %, at most 70 wt % or even at most 60 wt %, are preferred, as the presence of significant amounts of water inhibits self-condensation of the solvent and therefore loss of the non-hydrolytic solvent, which usually occur during organosolv conditions when using treatment liquids comprising greater amounts of non-hydrolytic solvent. Here, wt % values of water are given based on total weight of the solvents (i.e. non-hydroxylic solvent, water and optionally minor amounts of hydroxylic solvent) in the treatment liquid.

Minor amounts of other, i.e. hydroxylic, organic solvents, in addition to the non-hydroxylic organic solvent(s), may also be present. These can typically be alcohols such as ethanol. It was found that replacing part of the ethanol, which is commonly used during organosolv treatment of biomass, with a non-hydroxylic organic solvent already beneficially effects the results of the low temperature organosolv process. Preferably, the treatment liquid comprises at most 25 wt % hydroxylic, in particular alcoholic solvents, more preferably at most 10 wt %, even more preferably at most 2 wt %, most preferably no alcoholic organic solvent. Here, wt % values of hydroxylic solvent are given based on total weight of the solvents (i.e. non-hydroxylic solvent, water and hydroxylic solvent) in the treatment liquid. In an especially preferred embodiment, the treatment liquid consists of acetone, water and an acid, wherein the weight ratio acetone/water is preferably between 40/60 and 70/30.

During the organosolv reaction, acid is present to lower the pH. Typically, the pH during low temperature organosolv is between 0.5 and 7.0, preferably between 1.0 and 5.0, most preferably between 1.5 and 3.0. For optimum fractionation to cellulose pulp and lignin-containing liquor, the amount of acid present during organosolv is preferably between 5 mmol and 2.5 mol per kg dry weight of the biomass, more preferably between 50 mmol and 1 mol, most preferably between 100 and 750 mmol. Otherwise defined, the amount of acid is preferably between 0.5 and 250 g per kg dry weight of the biomass, more preferably between 0.5 and 100 g, even more preferably at least 5 and/or up to 100 g, most preferably at least 10 g and/or up to 75 g. Conveniently, the acid is comprised in the treatment liquid, but the acid may also be added separately to the suspension of biomass in the treatment liquid or to the biomass before the remainder of the treatment liquid is added.

Preferably, the concentration of the acid in the treatment liquid is between 1 mM and 200 mM, more preferably between 10 mM and 100 mM, most preferably 35-85 mM. In terms of weight, it is preferred that the treatment liquid comprises between 0.01 wt % and 2.0 wt % acid, more preferably between 0.05 wt % and 1.5 wt %, most preferably between 0.1 wt % and 1.0 wt %. Amounts of acid in the treatment liquid above the upper limits may result in more side-reactions, and thus the formation of more impurities, and in more solvent self-condensation and consequent loss of solvent, during organosolv. Lower amounts of acid, on the other hand, reduce the extent of fractionation and delignification realized by the present process. The inventors found that the above acid concentration ranges provide optimal results in that no or hardly any solvent self-condensation is observed, while delignification remains high. As the skilled person appreciates, the amount of acid which is used for optimum performance of the organosolv reaction may vary depending on the strength of the acid (pKa) and the acid neutralisation capacity of the biomass, as well as on the process conditions. Working at decreased L/S ratios favours an increase in acid concentration in the treatment liquid, but at the same a reduction in acid load per kg biomass. Preferred L/S ratios are given elsewhere in the specification.

Suitable acids include organic acids and inorganic acids. Preferred acids have a pKa value of 4.5 or lower, preferably a pKa value of 3.0 or lower, most preferably a pKa value of 1.0 or lower. Acids with such low pKa values are preferred, as a lower amount is needed to enable efficient organosolv fractionation of the biomass, when compared to acids having a higher pKa value. Suitable acids include sulfuric acid, sulfurous acid, hydrochloric acid, phosphoric acid, perchloric acid, sulfonic acids such as methanesulfonic acid and para-toluenesulfonic acid, formic acid, oxalic acid, benzoic acid, lactic acid, malonic acid, maleic acid, dichloroacetic acid, trichloroacetic acid, trifluoroacetic acid, and combinations thereof. As carboxylic acids are more prone to side-reactions than acids which do not comprise a carboxyl group, such as inorganic acids, the use of non-carboxylic acids or even inorganic acids is especially preferred. Thus, preferably the acid is selected from sulfuric acid, sulfurous acid, hydrochloric acid, phosphoric acid, para-toluenesulfonic acid, and combinations thereof. Most preferably, sulfuric acid is used. Herein, "the acid" may refer to a single compound, or to a mixture of different acids. Preferably, a single acid is used.

In a particularly preferred embodiment, the organosolv step is performed at a temperature of 130-160° C., preferably 130-150° C. and preferably for a duration of 60-150 min, using a treatment liquid comprising a non-hydroxylic ketone solvent, said ketone preferably comprising acetone, butanone or a mixture thereof, and water in a weight ratio of 40/60-70/30, preferably 40/60-60/40, and 10-100 mM, preferably 35-85 mM acid, preferably sulfuric acid.

Organosolv at reduced temperatures is accompanied with less side-reactions compared to organosolv at conventional temperatures. Less degradation of hemicellulose or xylose to undesired by-products (e.g. furfural and humins) and less formation of pseudo-lignins (e.g. by reaction of xylan and xylose degradation products with lignin) is observed. Importantly, low temperature organosolv using a non-hydroxylic organic solvent also gives less hemicellulose or xylose degradation to undesired by-products (e.g. xylosides) and less pseudo-lignin formation (e.g. by ethoxylation), compared to low temperature organosolv using an alcoholic organic solvent, in particular ethanol. During organosolv, certain amounts of monomeric sugars are formed at all times, such as glucose and xylose. Using low temperature organosolv with a non-hydroxylic organic solvent, fewer degradation products or by-products from monomeric sugars are observed. Glucosides and xylosides were produced at low levels only, if at all, contrary to low temperature organosolv with ethanol as solvent, and also minor amounts of hydroxymethylfurfural (from glucose) and furfural (from xylose) were detected. The formation of glucosides and xylosides is one of the major losses in biomass valorisation, as those compounds have limited economic value, compared to glucose and xylose, and are not easily converted to more valuable compounds. In addition, such fewer side-reactions also lead to a reduced solvent loss, which occurs when hydroxylic solvents react via their hydroxyl moiety with (monomeric) sugars or lignin. As such side-reactions do not occur for non-hydroxylic solvents, solvent loss is reduced to a minimum.

A major advantage of the organosolv process according to the present invention is the formation of product streams with higher purity (fewer impurities), when compared to prior art organosolv processes, and a higher yield in monomeric, oligomeric and polymeric saccharides. This is especially true in case the organosolv process according to the invention is combined with hydrolysis of the cellulose pulp, which converts polymeric and oligomeric saccharides to monomeric saccharides, as such obtaining high yields of monomeric saccharides based on total carbohydrates present in biomass.

Organosolv yields a cellulose pulp and a lignin-containing liquor. The lignin liquor obtained by the process according to the invention comprises a higher content of native lignin and a higher amount of xylose, when compared to prior art lignin liquors. Without being bound to any theory, it is envisioned that fewer reactions take place between lignin and e.g. cellulose or hemicellulose derivatives, degradation products thereof, or other reactive components present in the biomass such as proteins and other non-structural components, during the organosolv process according to the invention. These reactions are reduced in the process according to the invention by virtue of the reduced temperature of the organosolv reaction and the use of non-hydroxylic organic solvent. Hemicellulose or its monomeric derivatives are prone to degradation, and in view of this reduced degradation, less reaction of reactive degradation products with lignin occurs. The amount of hydroxyl moieties in the lignin (typically determined in mmol OH per g lignin) is a measure for the nativity of the lignin, i.e. the degree to which the lignin produced by the biomass treatment process resembles native lignin, in particular as far as its substitution pattern is concerned. The hydroxyl moieties present in native lignin may react with e.g. hemicellulose degradation products and non-structural components in the biomass (proteins, other extractives), under the conditions of the organosolv reaction. A reduced hydroxyl content thus indicates that more pseudo-lignin is formed. The process according to the invention affords lignin with an increased hydroxyl content, when compared to prior art process, both in view of the reduced temperature of the organosolv reaction and the use of a non-hydroxylic organic solvent.

Extraction

In one embodiment, the process according to the invention comprises one or more extraction steps, prior to being subjected to organosolv. In the context of the present invention, one or more extraction steps prior to organosolv are also referred to as "pre-extraction". Pre-extraction includes at least one aqueous extraction step and/or at least one organic extraction step. Without being bound by a theory, it is believed that extraction of the biomass prior to organosolv removes non-structural biomass components (extractives) which may hamper the organosolv process and/or the subsequent enzymatic cellulose hydrolysis. In view of the many side-reactions that occur when low temperature organosolv is performed using a hydroxylic solvent, performing such a pre-extraction may be preferred.

In the context of the present invention, "organic extraction" refers to extraction with an extraction liquid comprising at least 20 wt % of one or more organic solvents, preferably at least 50%, more preferably at least 70%, and thus at most 80 wt % water, preferably at most 50%, more preferably at most 30%. Likewise, "aqueous extraction" refers to extraction with an extraction liquid comprising at least 80 wt % water, and thus at most 20 wt % of one or more organic solvents. In one embodiment, only one extraction step is performed prior to organosolv, wherein the biomass is extracted with an extraction liquid comprising a first organic solvent, optionally as a mixture with water. Alternatively, extraction involves multiple extraction steps, each with a different extraction liquid comprising water, one or more organic solvents or mixtures thereof Herein, multiple extractions with the same extraction liquid are referred as a single extraction step. Thus, in case extraction is performed prior to organosolv, extraction may involve at least one, at least two, at least three, or at least four separate extraction steps. In one embodiment, at least one aqueous extraction step is performed prior to organosolv, using water as extraction liquid (i.e. containing less than 20% of organic solvent). In an alternative embodiment, at least one aqueous extraction step is performed prior to organosolv, using water as extraction liquid (i.e. containing less than 20% of organic solvent), and at least one organic extraction step is performed using an extraction liquid comprising at least 20%, preferably at least 50%, more preferably at least 70% of an organic solvent.

In the process according to the invention, side-reactions are avoided when using a non-hydroxylic solvent, and thus in one embodiment it is advantageous not to employ a pre-extraction step prior to low temperature organosolv fractionation. In one embodiment, no organic pre-extraction is performed and no or only an aqueous pre-extraction is performed. Nevertheless, as pre-extraction may result in an even better performance of the organosolv step itself and a more efficient enzymatic hydrolysis of cellulose and thus a further reduction of the required enzyme load and associated costs, performing one or more aqueous and/or organic pre-extraction steps is not excluded from the process of the invention.

Suitable organic solvents to be used in organic pre-extraction include, but are not limited to, lower alcohols and diols, ethers, ketones, amides, lower alkanes, carboxylic acids and $CO_2$ (supercritical: sc). In the context of the present invention, $CO_2$ (sc) is considered an organic solvent, in view of its suitability in organic pre-extraction. Herein, "lower" means containing 1-6 carbon atoms ($C_1$-$C_6$), especially $C_2$-$C_4$ for alcohols, and especially $C_3$-$C_5$ for other solvents including ketones, ethers, esters and amides. The organic solvent is preferably water-miscible or capable of dissolving at least 10 wt % of water. Examples of suitable organic solvents to be used in organic pre-extraction include methanol, ethanol, propanol, isopropanol, butanol and its isomers, ethylene glycol, propylene glycol, methoxyethanol, dimethoxyethane, diethylene glycol, dioxane, acetone, methyl ethyl ketone, tetrahydrofuran, dimethyl formamide, dimethyl acetamide, N-methylpyrrolidone etc. Further polar (co)solvents can be used as well, although these are slightly less preferred, for example acetonitrile, formic acid, acetic acid, methyl acetate, ethyl acetate and non-apolar haloalkanes such as dichloromethane. Apolar solvents, such as $CO_2$ (sc) or hydrocarbons, e.g. pentane, cyclopentane, hexane, toluene or mixtures thereof, such as petroleum ether, can be also used as (co)solvents, or as solvents in an optional additional extraction step. In the context of the present invention, mixtures of miscible organic solvents are also encompassed in the term "organic solvent". Preferably, the organic solvent to be used in organic pre-extraction is selected from methanol, ethanol, propanol, butanol and acetone, more preferably from methanol, ethanol and acetone. It may be advantageous useful to use the same organic solvent for pre-extraction as is used as non-hydroxylic organic solvent in the treatment liquid.

The aqueous pre-extraction step is conveniently performed using (non-demineralised) tap water or filtered, relatively clean water, while demineralised water is also suitable, with at most 20 wt % added organic solvents or other additives, preferably without added organic solvents or other additives. Aqueous pre-extraction steps may be performed using an aqueous extracting liquid, in particular water. The aqueous liquid may contain agents assisting in the dissolution of extractives, such as acids, bases, salts and surfactants. The pH may be from slightly alkaline to acidic, e.g. between 2 and 10, preferably between 4 and 8. If desired minor amounts of an organic solvent (e.g. as described above for the organic extraction) may be added to the aqueous extracting liquid. However, the level of organic solvents is preferably kept low, e.g. below 20 wt %, more preferably below 10 wt %, most preferably below 2 wt %.

Each individual extraction step of the extraction may be performed using any extraction technique known in the art. Conveniently, extraction is performed by washing the biomass with the extraction liquid, or by soaking the biomass in the extraction liquid. In this embodiment, the biomass preferably soaks at least 1 minute in the extraction liquid, more preferably between 5 minutes and 600 minutes, most preferably between 10 minutes and 120 minutes. The extraction may also be performed stage-wise, in a counter-current mode. In such a staged mode, relatively clean extraction liquid is used for a second or later stage of the extraction and the extract of the second or later stage is used as an extraction liquid for the preceding (or first) stage. In this way the residual amount of extractives in the biomass is minimized while keeping the amount of extraction liquid relatively low. Counter-current extraction allows a reduction in the total amount of extraction solvent.

Each extraction step of the extraction can be performed with water and/or first organic solvent as extracting liquid, wherein the extracting liquid has a temperature between its melting temperature and its boiling temperature (or higher if pressurized), i.e. is in liquid form. Preferred extracting temperatures are from 10 to 100° C. For aqueous extraction steps, the extraction temperature is more preferably from 15 to 75° C., most preferably from 20 to 60° C., and for organic extraction steps more preferably from 15 to 80° C., most preferably from 30 to 75° C. For extraction steps using a mixture of water and organic solvent(s), the skilled person will appreciate how to manipulate the temperatures for optimal results. For each individual extraction step, the amount of extraction liquid is preferably between 0.1 L and 25 L of liquid per kg of biomass. For single stage organic extraction, the preferred amount of extraction liquid is between 0.1 L and 12 L, most preferred between 0.5 L and 6 L of solvent per kg of biomass. For single stage aqueous extraction, the preferred amount of extraction liquid is between 0.1 L and 12 L, most preferred between 0.5 L and 10 L of solvent per kg of biomass. For counter-current extraction, the preferred amount of extraction liquid is between 0.1 L and 6 L, especially between 0.5 L and 4 L solvent per kg biomass. The biomass weight is understood herein as the dry weight, without adherent water.

The mixture of biomass and extraction liquid may be filtered after each extraction step of the extraction, using a filter having small enough pores to retain the chopped and washed or soaked biomass, and large enough pores to allow the extract comprising extractives to pass. Typically, the pores of such a filter are between 10 μm and 10 mm in diameter, preferably between 100 μm and 1 mm. The retentate comprising biomass is used for further treatment by organosolv as described below.

During extraction, the total dry weight of the biomass may reduce, as water-soluble and/or organic solvent-soluble components will be washed away. These extractives may include salts, proteins, fatty acids, triglycerides, waxes, terpenes and resin acids. As the skilled person will appreciate, hydrophilic components (e.g. salts, water-soluble proteins) will predominantly be washed away during aqueous extraction, i.e. in the pre-extraction step, while lipophilic components are predominantly extracted during extraction with an organic solvent. The composition and concentration of washable components is highly dependent on the type of biomass. For example, annual fibres such as straw contain relatively large amounts of fatty acids and/or waxy materials, which may be extracted using organic solvent, and (soft)wood may contain significant amounts of terpenes and resin acids.

Enzymatic Hydrolysis

In a preferred embodiment, the cellulose-enriched product stream (pulp), which is obtained as a product from the organosolv step, is subjected to enzymatic hydrolysis. Enzymatic hydrolysis of cellulose to glucose is accomplished by an enzyme or combination of enzymes capable of hydrolysing cellulose, referred to as hydrolytic enzymes, preferably cellulases. Hydrolysis of cellulose is also known as cellulolysis. The activity of cellulase enzymes is typically measured in FPU (filter paper unit); see Ghose, T. K. Measurement of cellulase activities. *Pure Appl. Chem.* 1987, 59, 257-268. The process according to the invention may be performed using any cellulase enzyme. Suitable cellulase enzymes are endocellulases (cleaving cellulose at inner positions), exocellulases (cleaving cellulose at more external positions to produce cellobiose or cellutetraose), beta-glucosidases (cellobiases, cleaving the exocellulase products into glucose units). Other cellulase enzymes, such as oxidative cellulases and cellulose phosphorylases, are less preferred. Preferably a combination of cellulase enzymes is used, in particular a combination of endo-cellulase, exocellulase and β-glucosidase. Also, hemicellulases (e.g. xylanases, arabinases, mannanases, etc.) may be present to decompose any residual hemicellulose remaining after the organosolv step.

In the process according to the invention, the enzymatic hydrolysis of cellulose may be performed in any manner known in the art. Thus, the cellulose-enriched product stream or cellulose-rich pulp is brought in contact with an enzyme capable of hydrolysing cellulose, preferably a mixture of cellulases. The resulting hydrolysate is rich in glucose, which may be further processed, optionally after separation of solid residues, such as fermented to produce e.g. ethanol or other alcohols, or thermally or chemically treated to produce e.g. 5-hydroxymethyl-furfural and other furans, or the glucose may be used as such, as known in the art.

In case an aqueous pre-extraction step (i.e. the extracting liquid comprises below 20 wt % organic solvent) is part of the process according to the invention, the aqueous extract, in particular a protein-containing aqueous extract, obtained by aqueous pre-extraction, is beneficially used as supplement during enzymatic hydrolysis of the cellulose pulp. The presence of such an aqueous extract, optionally after (partial) concentration by methods known in the art, results in significant enhancement of the enzyme activity during enzymatic hydrolysis of cellulose. As such, the enzyme loading during enzymatic hydrolysis step can be significantly reduced, without negatively affecting the yield of glucose and/or the rate of glucose formation. Surprisingly, the protein-rich aqueous biomass extract, suitable for enhancing the activity of the hydrolysing enzyme, may efficiently be prepared by extracting the biomass with water and subsequently filtering the mixture. No further purification steps of the extract are necessary for achieving a significant increase in enzyme activity during enzymatic hydrolysis. Other components, which may be co-extracted from the biomass during aqueous extraction, do not inhibit the hydrolytic enzyme (cellulase) during enzymatic hydrolysis of cellulose, or this inhibition is more than compensated by the activity raise caused by the presence of the aqueous extract. Protein from the biomass itself constitutes a relatively cheap and easily accessible protein source.

As a result of the (further) reduced enzyme requirement, this preferred embodiment of the process according to the invention meets the need for reducing the costs of enzymatic hydrolysis of cellulose. Without being bound to a theory, the inventors assume that proteins from the aqueous extract are adsorbed to the lignin present in the cellulosic substrate. As such, the amount of hydrolytic enzyme inactivated by adsorption onto liberated lignin decreases. Thus, a cellulose-rich pulp, originating from pretreated biomass is contacted simultaneously with (i) an enzyme capable of hydrolysing cellulose, preferably a (mixture of) cellulase(s), and with (ii) a protein-rich aqueous extract originating from aqueous extraction of biomass. In an especially preferred embodiment, the biomass is subjected to aqueous pre-extraction, and optionally organic pre-extraction, and subsequently subjected to pretreatment according to the present invention, i.e. subjected to organosolv as described herein, and the protein-rich aqueous biomass extract used during the enzymatic hydrolysis of biomass originates from aqueous extraction of the same biomass, prior to organosolv. The protein-rich extract may be the directly obtained extract or a concentrate thereof.

Further Process Steps

The liquor, resulting from separating off the cellulose-enriched pulp, may be further treated or separated for the purpose of isolating other valuable products. In particular, the liquor, containing lignin, carbohydrates (notably hemicellulose and its degradation products), organic acids, salts and other compounds, may be depleted in lignin by precipitation of lignin through decreasing the organic solvent content of the liquor, e.g. by dilution with water and/or by evaporation of (non-hydroxylic and/or other) organic solvent, e.g. followed by centrifugation. Alternatively, the ratio within a mixture of organic solvents may be altered, which may lead to phase separation between the aqueous and organic phases, facilitating the separation which may e.g. be performed by decantation. This is particularly practical in case a mixture of solvents is used as non-hydroxylic organic solvent. Reducing the acetone content (e.g. by evaporation) or increasing the butanone content (e.g. by addition thereof) leads to such phase separation. The resulting liquid aqueous stream, which is depleted in lignin, and which contains appreciable levels of hemicellulose derivatives, e.g. xylose and its oligomers and polymers, may advantageously be subjected to process steps for recovering or valorising these carbohydrates, e.g. by anaerobic treatment using an anaerobic culture from commercial anaerobic digestions or fermentations as a starting sludge. The temperatures used in the anaerobic treatment are typical for mesophilic micro-organisms, i.e. between 15 and 55° C., preferably between 30 and 45° C. Biogas can be collected from the anaerobic treatment. Alternatively, anaerobic fermentation can be performed for converting the hemicellulose decomposition products and possible other organic products to ethanol or other alcohols, by using yeasts capable of converting sugars to alcohols and carbon dioxide. The yeast may advantageously have been engineered to be capable of converting other specific sugars (e.g. xylose) from hemicelluloses to alcohols as well, e.g. by introducing xylose-isomerase and/or arabinose-converting enzymes into the yeast (see e.g. WO 03/062430, WO 2008/

041840, WO 2010/074577). Alternative purposes of these carbohydrates originating from hemicellulose include surfactant, sugar alcohol or furan production.

EXAMPLES

Example 1

Lignin Solubility in Ketone Solvents

Lignin (prepared via the Alcell process, see Pye and Lora, *Tappi* 1, 1991, 74, 113-118) was dissolved at room temperature in several solvent systems that are suitable as treatment liquid for an organosolv step. For the ethanol/water solvent system, 100 g lignin was mixed with 1 L solvent, and for the ketone/water solvent systems, 500 g lignin was mixed with 1 L of solvent. The solubility of lignin is given in Table 2 below.

TABLE 2

Lignin solubility in several solvent systems

| Solvent system (w/w) | Lignin solubility |
| --- | --- |
| ethanol/water (60/40) | 66 g/kg solvent |
| acetone/water (60/40) | 548 g/kg solvent |
| acetone/butanone/water (20/40/40) | 496 g/kg solvent |

Example 2

Low Temperature Organosolv with Acetone

Wheat straw was chopped into pieces of about 1 cm length, and was divided into eight batches which received different treatments as summarised in Table 3. Pre-extraction was performed on batches 2, 5 and 7, which involved extraction with 10 L water per kg biomass, and subsequently with 10 L ethanol or acetone per kg of the original biomass prior to aqueous extraction. Batches 1-8 were subsequently subjected to organosolv at the indicated temperature, using the solvent system and treatment time as given in Table 3. The liquid/solid ratio was 10 L per kg biomass. Sulfuric acid was added to the treatment liquid of batches 1-7. The increased $H_2SO_4$ concentration for the batches which did not undergo pre-extraction (1, 3, 4, 6) was applied to counteract the higher acid-neutralisation capacity of the mineral part of the original biomass, which is otherwise lowered during pre-extraction by (partial) removal of the mineral part. For batch 8, no acid was added, and organosolv was performed auto-catalytically at a temperature of 205° C.

TABLE 3

Pre-extraction and treatment conditions of wheat straw

| | | organosolv | | | |
| --- | --- | --- | --- | --- | --- |
| batch | pre-extraction | t (min) | T (° C.) | solvent system (w/w) | $H_2SO_4$ (mM) |
| 1 | no | 120 | 140 | ethanol/water (60/40) | 60 |
| 2 | water; ethanol | 120 | 140 | ethanol/water (60/40) | 50 |
| 3 | no | 120 | 140 | acetone/water (50/50) | 60 |
| 4 | no | 60 | 140 | acetone/water (50/50) | 60 |
| 5 | water; acetone | 60 | 140 | acetone/water (50/50) | 50 |
| 6 | no | 60 | 140 | acetone/water (60/40) | 60 |
| 7 | water; acetone | 60 | 140 | acetone/water (60/40) | 50 |
| 8 | no | 60 | 205 | acetone/water (50/50) | 0 |

During organosolv with ethanol/water as treatment liquid (batch 1), the formation of balls of fatty acids and/or waxy material was observed, which hindered the fractionation of straw into the lignin-enriched liquor and the cellulose-enriched pulp, giving i.a. rise to a lower glucan concentration in the pulp. Only when pre-extracted biomass was subjected ethanol/water organosolv (batch 2), no waxy balls were observed. In batches 3-7, which are according to the invention and wherein acetone/water was used as treatment liquid, no such balls were observed for both the pre-extracted and non-pre-extracted wheat straw.

The results of the organosolv regarding the pulp are given in Table 4. Pulp yields, delignification percentages and pulp compositions are acceptable for all experiments, although for the ethanol organosolv (not according to the invention), the additional step of pre-extracting the biomass gave a higher glucan purity of the pulp. Reducing the reaction time from 120 to 60 minutes of acetone organosolv (batches 3 vs. 4) gave surprisingly similar results in terms of delignification and pulp compositions, while pulp yield increases. High temperature organosolv (batch 8) gave similar results in terms of pulp composition and delignification, indicating that reducing the temperature does not negatively affect the performance of the organosolv fractionation. The form of the lignin (hydroxyl content) obtained as precipitate from the liquor obtained after organosolv is also given in Table 4. First of all, the lignin obtained by low temperature organosolv with acetone shows an increased content of hydroxyl groups, when compared to low temperature organosolv with ethanol as solvent, indicative of more native lignin and reduced formation of pseudo-lignins. In addition, the hydroxyl content of the lignin is markedly increased when compared to lignin obtained with high temperature organosolv at about 200° C. The hydroxyl content of the lignin was determined via the wet chemical method as described by Zakis et al., "Functional analysis of lignins and their derivatives", TAPPI Press, Atlanta, 1994, page 94.

Compositions were determined using the method described in W. J. J. Huijgen, A. T. Smit, P. J. de Wild, H. den Uil, *BioResource Technology*, 2012, 114, 389-398. Therein, glucan, xylan and other polysaccharides were determined by hydrolysis and monosaccharide analysis and thus include any hydrolysis products (oligomers and monomers). The four components given in Table 4 make up approximately 90 wt % of the pulp, and the remaining 10 wt % may include (precursors of) sugar monomers (including arabinose, galactose, mannose and rhamnose), uronic acids and extractives (non-structural components such as peptides, lipids, DNA, chlorophyll).

TABLE 4

Pulp yield and composition, hydroxyl content of lignin

| batch | pulp yield (wt %)[a] | delignification (%)[b] | OH[c] | pulp composition (wt %)[d] | | | |
|---|---|---|---|---|---|---|---|
| | | | | glucan | xylan | lignin | ash |
| 1 | 50.4 | 73.9 | 6.0 | 63.8 | 8.5 | 9.2 | 6.8 |
| 2 | 40.2 | 87.5 | 6.4 | 78.9 | 3.5 | 5.5 | 4.6 |
| 3 | 43.0 | 73.1 | 6.9 | 73.9 | 3.1 | 11.0 | 3.2 |
| 4 | 50.1 | 69.8 | 6.7 | 68.6 | 6.5 | 10.6 | 5.3 |
| 5 | 43.0 | 82.1 | 7.9 | 75.8 | 3.9 | 7.3 | 6.0 |
| 6 | 48.6 | 74.2 | 5.7 | 69.1 | 5.6 | 9.4 | 6.5 |
| 7 | 42.0 | 84.3 | 7.0 | 77.8 | 3.2 | 6.6 | 4.9 |
| 8 | 48.7 | 78.6 | nd | 65.4 | 7.8 | 7.0 | 11.1 |

[a]Based on dry weight of the fresh biomass, before pre-extraction.
[b]Reduction in lignin content in pulp compared to fresh biomass.
[c]OH content in mmol per g lignin; nd = not determined.
[d]Based on dry weight of cellulose pulp.

Some xylan and glucan degradation products were detected in the lignin-containing liquor. The products obtained from xylan and glucan are given in Table 5, in xylose and glucose equivalents respectively. In general, more residual xylan is found in the pulp when no pre-extraction is performed, when ethanol is used instead of acetone (batches 1 and 2), and when organosolv is performed at high temperature without acid (batch 8). The hydrolysis and degradation products of xylan are found in the liquor. Importantly, the yield of monomeric xylose is greatly increased when ethanol is replaced by acetone since no ethyl xylosides are formed using low temperature organosolv with acetone. Some furfural is detected in all liquors. Most, if not all of the remaining hemicellulose will have been converted to soluble xylo-oligosaccharides (XOS), which end up in the liquor, or to undesirable condensation products such a lignine-furfural condensation products and humins which are expected to be formed at the higher temperature used in the organosolv reaction of batch 8.

Regarding the glucan products, the major difference between ethanol and acetone as organic solvent is the formation of glucosides in the hydroxylic solvent, while no ethylglucosides are formed using the non-hydroxylic solvent. The most significant effect associated with reducing the temperature of the organosolv reaction from 205° C. to 140° C. is the increase in xylose yield, while the xylan hydrolysis degree remains more or less the same. This indicates that xylan degrades beyond its monomeric sugars at high temperature into undesirable by-products which have not been measured. Likewise, glucan is degraded to some extent at high temperature, which is not found as glucose monomers or HMF. Thus, the glucose monomers that are formed during organosolv degrade into undesirable by-products at 205° C.

TABLE 5

Distribution of xylan and glucan products

| batch | xylan (%)[a] | | | | glucan (%)[b] | | | |
|---|---|---|---|---|---|---|---|---|
| | xylan | Xyl | furfural | EX | glucan | Glc | HMF | EG |
| 1 | 21.5 | 32.9 | 7.7 | 38.1 | 90.7 | 2.5 | bdl | 4.6 |
| 2 | 7.2 | 36.9 | 11.1 | 46.6 | 89.5 | 3.0 | bdl | 5.4 |
| 3 | 6.8 | 81.3 | 15.4 | — | 89.8 | 7.3 | 0.8 | — |
| 4 | 16.4 | 73.2 | 7.3 | — | 97.2 | 5.6 | 0.5 | — |
| 5 | 8.4 | 76.7 | 9.7 | — | 92.1 | 5.6 | 0.3 | — |
| 6 | 13.6 | 71.9 | 9.4 | — | 94.8 | 5.7 | 0.5 | — |
| 7 | 6.7 | 70.2 | 12.6 | — | 92.4 | 6.0 | 0.5 | — |
| 8 | 17.7 | 0.6 | 3.8 | — | 92.0 | bdl | 0.2 | — |

[a]In xylose equivalents; moles of product based on total moles of xylose monomeric units present in xylan in the fresh biomass, before pre-extraction. Total percentages above 100% result from measuring inaccuracies. Xylan is found in the pulp, the rest in the liquor. Xyl = xylose; EX = ethyl xylosides;
[b]In glucose equivalents; moles of product based on total moles of glucose monomeric units present in glucan in the fresh biomass, before pre-extraction. Total percentages above 100% result from measuring inaccuracies. Glucan is found in the pulp, the rest in the liquor. Glc = glucose; HMF = 5-hydroxymethyl-furfural; EG = ethyl-glucosides; bdl = below detection limit.

Figure 1:
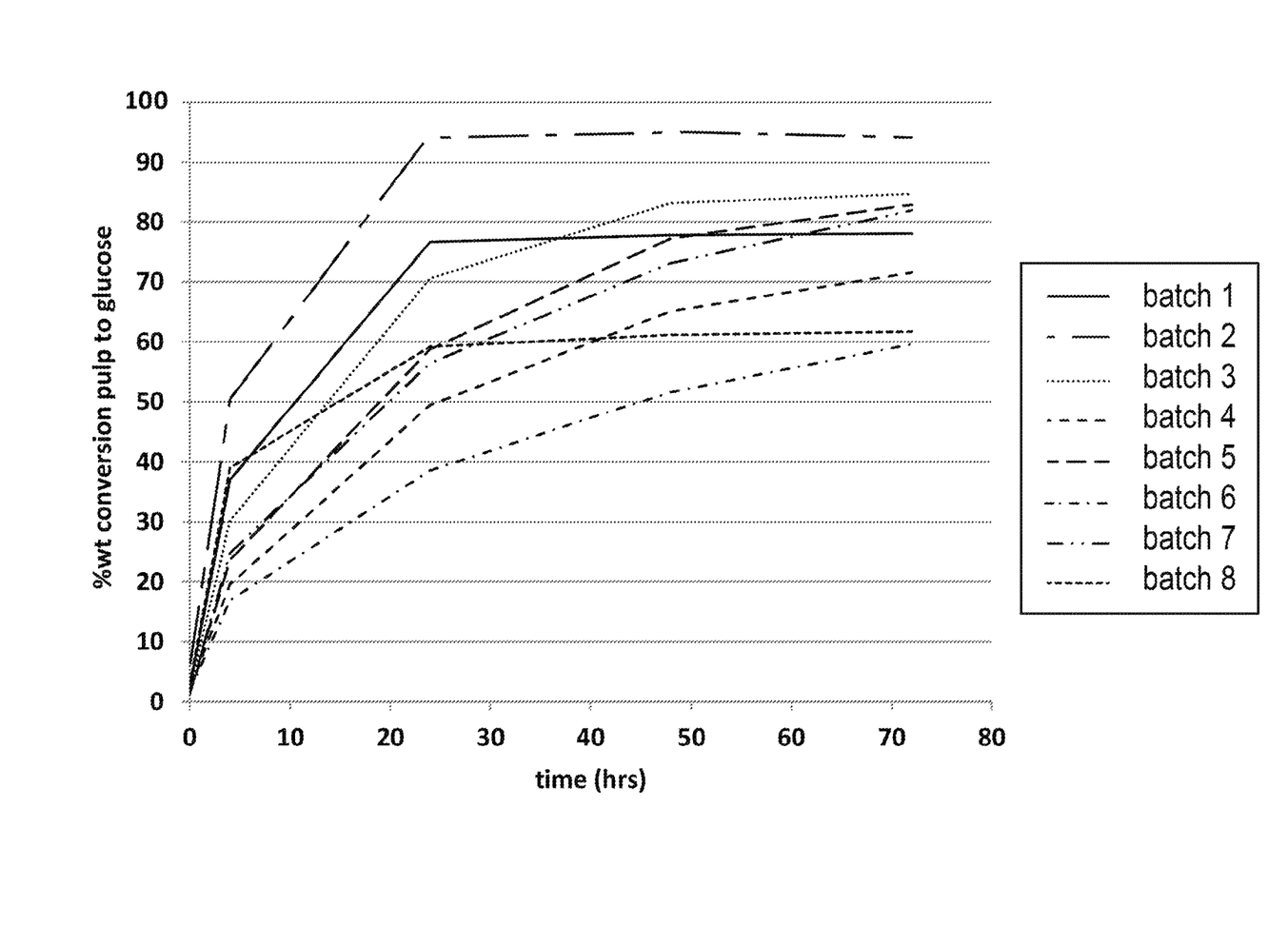
FIG. 1 summarizes the results obtained using the cellulose-enriched pulp obtained by organosolv of batches 1-8.

The cellulose-enriched pulp obtained by organosolv fractionation of each of the batches was subsequently subjected to enzymatic hydrolysis. Conditions: 10 FPU per gram pulp (for batches 1 and 2: 20 FPU/g, for batch 8: 38 FPU/g) of cellulase enzyme (Accellerase 1500 (batches 1-7) or Accellerase 1000 (batch 8), DuPont Industrial Biosciences); 1.50 g pulp (dry weight) per 50.0 mL water buffered at pH 4.8; time=72 h. The progress of the enzymatic hydrolysis was monitored by determination of the glucose yield (as wt % based on total dry weight of the pulp at t=0 h) at various intervals up to t=72 h. The figure summarises the results obtained using the cellulose-enriched pulp obtained by organosolv of batches 1-8. Maximum glucose conversion values for batches 1, 2 and 8 were obtained after 24 h, in view of the increased enzyme load. The cellulose pulp obtained by organosolv at reduced temperatures is readily hydrolysed with a relatively low enzyme load of 10 FPU/g. Batches 4-7, subjected to low temperature organosolv with acetone for 60 minutes, were hydrolysed more or less similarly to batch 3 which was subjected to organosolv for 120 minutes. From a cost-effectiveness point of view, it is beneficial to perform the organosolv reaction for a shorter period of time, for which the process according to the invention is well suited. The pulp obtained with high temperature organosolv gave a lower yield in glucose, especially since the final conversion was already obtained after 24 h, while the other batches did not reach the final glucose conversion at the end of the measurement at t=72 h. The pulp obtained by ethanol organosolv of non-pre-extracted biomass (batch 1) gave slightly lower glucose yield than the pulp obtained by acetone organosolv of batches 3, 5 and 7, especially in view of the expected further conversion of these batches after t=72 h. The pulp obtained from ethanol organosolv of pre-extracted biomass (batch 2) gave the highest glucose yield, based on total weight of the pulp, which is due to its high glucan content (see Table 4) and a higher enzyme load. However, the total glucose yield based on the glucan present in the fresh biomass is more or less similar for all experiments. Thus, it is concluded that the organosolv process is efficiently performed at reduced temperatures, such as at 140° C. or lower, using acetone as organic solvent, and that the cellulose pulps obtained therewith are efficiently hydrolysed to glucose.

Example 3

Low Temperature Organosolv with Ethyl Levulinate

Wheat straw was chopped into pieces of about 1 cm length, and was divided into three batches which were subsequently subjected to organosolv at 140° C. for 120 min, using the solvent system as given in Table 6. The liquid/solid ratio was 10 kg per kg biomass. 60 mM of sulfuric acid was added to the treatment liquid. Replacing ethanol for ethyl levulinate as the organic solvent did not significantly affect the pulp yield, but gave a rise in lignin yield, determined as amount of lignin precipitated upon a three-times dilution of the liquor with water having a temperature of about 5° C., based on total weight of lignin present in the biomass. Using ethyl levulinate as a solvent resulted in a larger share of lignin that ended up in the liquor. From the unchanging pulp yield and the increase in lignin yield in the liquor, it can be concluded that the pulp contains an increasing content of glucan, with increasing ethyl levulinate content in the treatment liquid.

Tables 7 and 8 give the yields of the (degradation) products of xylan and glucan formed during organosolv. When ethanol is replaced by ethyl levulinate, less xylosides and glucosides were formed during low temperature organosolv, and the content of monomeric sugars increased, indicative of less degradation or further reaction of hemicellulose and cellulose beyond their monomers.

TABLE 6

Organosolv conditions and results of wheat straw

| batch | solvent system (w/w)[a] | pulp yield (%)[b] | lignin yield (%)[c] |
|---|---|---|---|
| 1 | ethanol/water (50/50) | 47.0 | 50.2 |
| 2 | ethanol/EL/water (40/10/50) | 46.2 | 56.1 |
| 3 | EL/water (50/50) | 45.4 | 69.8 |

[a]EL = ethyl levulmate
[b]Based on dry weight of the fresh biomass.
[c]Amount of lignin precipitated, based on total weight of lignin in the fresh biomass.

TABLE 7

Xylan degradation products observed in liquor[a]

| batch | xylose | arabinose | furfural | xylosides |
|---|---|---|---|---|
| 1 | 33.6 | 4.2 | 6.3 | 26.2 |
| 2 | 34.9 | 4.6 | 7.4 | 24.5 |
| 3 | 50.7 | 6.7 | 15.2 | 11.7 |

[a]In wt % based on dry weight of xylan in the fresh biomass.

TABLE 8

Glucan degradation products observed in liquor[a]

| batch | glucose | galactose | glucosides | HMF | EMF |
|---|---|---|---|---|---|
| 1 | 2.8 | 1.0 | 3.2 | 0.3 | 0.1 |
| 2 | 2.7 | 1.0 | 2.8 | 0.3 | bdl |
| 3 | 5.1 | 1.5 | 1.6 | 0.5 | bdl |

[a]In wt % based on dry weight of glucan in the fresh biomass.
HMF = 5-(hydroxymethyl)furfural; EMF = 5-(ethoxymethyl)furfural; bdl = below detection limit.

Example 4

Low Temperature Organosolv with Acetone/Butanone Mixtures 280 g of dried beech wood was subjected to organosolv at 140° C. for 120 min, using the acetone/butanone/water 20/40/20 (w/w/w) as solvent system in a liquid to solid ratio of 4.3 kg treatment liquid to 1 kg biomass (dry weight). Sulfuric acid up to a concentration of 60 mM was added to the treatment liquid.

The pulp yield after organosolv amounted to 41.3 wt %, with a delignification of 87.8% (both calculated as in Table 4). The pulp contained 78.8 wt % glucan, 2.3 wt % xylan and 7.3 wt % lignin, based on dry weight of the pulp. Such excellent results, in terms of delignification and pulp composition, demonstrate that the use of (mixtures) of aqueous and non-hydroxylic solvents enables efficient organosolv fractionation of biomass at low temperatures and low L/S ratios.

The invention claimed is:

1. A process for fractionating lignocellulosic biomass and converting hemicellulose into xylose, the process comprising treating the biomass with a treatment liquid at a temperature of 100° C.-160° C., wherein the treatment liquid comprises:
    (i) 20-70 wt % of non-hydroxylic organic solvent comprising an ether and/or a carbonyl moiety;
    (ii) 20-80 wt % of water; and
    (iii) 0.5-100 g acid per kg biomass, and
    wherein the treating yields a pulp comprising cellulose and a liquor comprising lignin and xylose.

2. The process according to claim 1, wherein the non-hydroxylic organic solvent comprises ketones.

3. The process according to claim 2, wherein the non-hydroxylic organic solvent is acetone.

4. The process according to claim 1, wherein the treatment liquid comprises:
    (i) 30-60 wt % of a non-hydroxylic organic solvent comprising an ether and/or a carbonyl moiety;
    (ii) 40-70 wt % of water; and
    (iii) 5-75 g acid per kg biomass.

5. The process according to claim 1, wherein the treatment liquid comprises a weight ratio of organic solvent(s) to water between 40/60 and 65/35.

6. The process according to claim 1, wherein the treatment liquid comprises between 0.01 wt % and 2.0 wt % of the acid.

7. The process according to claim 1, wherein the acid has a pKa value of 4.5 or lower.

8. The process according to claim 1, wherein the acid is sulfuric acid.

9. The process according to claim 1, wherein the lignocellulosic biomass is selected from the group consisting of herbaceous biomass, softwood, hardwood, and combinations thereof.

10. The process according to claim 9, wherein the lignocellulosic biomass comprises herbaceous biomass.

11. The process according to claim 9, wherein the lignocellulosic biomass is herbaceous biomass and/or hardwood.

12. The process according to claim 1, wherein the treatment is performed at a liquid to solid ratio (L/S) below 12/1.

13. The process according to claim 12, wherein the L/S ratio is below 8/1.

14. The process according to claim 1, further comprising extracting the biomass with an extracting liquid at a temperature below 100° C. prior to the treatment step, wherein the extracting liquid comprises water and/or an organic solvent.

15. The process according to claims 14, wherein the extracting liquid comprises at least 80 wt % water.

16. The process according to claim 15, wherein the extracting liquid comprises at least 50 wt % of an organic solvent.

17. The process according to claim 16, wherein the organic solvent is selected from $C_2$-$C_4$ alcohols and $C_3$-$C_5$ ketones.

18. The process according to claim 1, wherein a cellulose-enriched pulp is obtained, which pulp is subjected to enzymatic hydrolysis.

19. The process according to claim 18, wherein the enzymatic hydrolysis yields a hydrolysate which is subjected to fermentation.

* * * * *